United States Patent [19]

Nagato et al.

[11] Patent Number: 4,634,784
[45] Date of Patent: Jan. 6, 1987

[54] PROCESS FOR PRODUCTION OF EPICHLOROHYDRIN

[75] Inventors: Nobuyuki Nagato; Hideki Mori; Kenichiro Maki; Ryoji Ishioka, all of Kawasaki, Japan

[73] Assignee: Showa Denko Kabushiki Kaisha, Japan

[21] Appl. No.: 741,053

[22] Filed: Jun. 4, 1985

[30] Foreign Application Priority Data

Jun. 4, 1984 [JP] Japan ................................. 59-113172

[51] Int. Cl.⁴ ........................................... C07D 301/26
[52] U.S. Cl. .................................................... 549/521
[58] Field of Search ......................... 568/850; 549/521

[56] References Cited

FOREIGN PATENT DOCUMENTS

| 1412886 | 8/1965 | France | 549/521 |
| 924458 | 4/1963 | United Kingdom . | |
| 1065496 | 4/1967 | United Kingdom | 568/850 |

OTHER PUBLICATIONS

Chemical Abstracts, 101:191136k and 191137m.

Primary Examiner—Norma S. Milestone
Attorney, Agent, or Firm—Sughrue, Mion, Zinn, Macpeak, and Seas

[57] ABSTRACT

A process for producing epichlorohydrin comprising the steps of:
(a) reacting allyl alcohol with chlorine at a temperature of −30° C. to 20° C. under a pressure of 0 to 10 atm (gauge) in an aqueous hydrogen chloride solution containing more than 45% but not more than 70% by weight of hydrogen chloride to form 2,3-dichloro-1-propanol;
(b) separating at least a portion of the hydrogen chloride by heating the reaction mixture obtained at step (a) to recover the hydrogen chloride in the form of gas;
(c) recycling the hydrogen chloride recovered at step (b) to step (a);
(d) separating the resultant liquid mixture after recovering at least the portion of the hydrogen chloride at step (b) into an aqueous phase and an oil phase by cooling the resultant liquid mixture to a temperature of 40° C. or less;
(e) recycling at least a portion of the separated aqueous phase at step (d) to step (a); and
(f) reacting the oil phase separated at step (d) directly or after increasing the purity of 2,3-dichloro-1-propanol contained in the oil phase by a separation operation with an aqueous alkaline solution or suspension at a temperature of 40° C. to 110° C. to form epichlorohydrin.

According to this process, the desired epichlorohydrin can be industrially and advantageously produced at a high yield and selectivity.

2 Claims, 1 Drawing Figure

PROCESS FOR PRODUCTION OF EPICHLOROHYDRIN

BACKGROUND OF THE INVENTION

1. Field of the Invention

The present invention relates to a process for producing epichlorohydrin useful as, for example, a solvent in various fields, a raw material for the production of epoxy resin and synthetic rubber, and a stabilizer for chlorinated rubber.

2. Description of the Related Art

Hitherto, epichlorohydrin has been typically produced, as shown in the following reaction equations (1), (2), and (3), by the subsequent steps: allyl chloride synthesis step (1) from the chlorination reaction of propylene, dichloropropanol synthesis step (2) from the chlorohydrination reaction of the allyl chloride, and epichlorohydrin synthesis step (3) from the saponification reaction of the dichloropropanol.

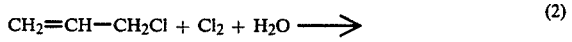

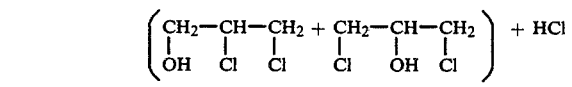

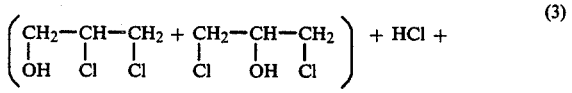

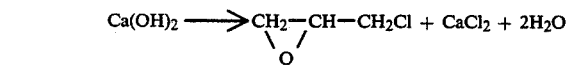

However, the above-mentioned production process of epichlorohydrin has serious problems from the practial point of view as follows:

(A) The first step (1) is generally carried out in the absence of a catalyst in a vapor phase. However, this step (1) has disadvantages, especially from the industrial standpoint, that (i) since the reaction temperature is high, the yield of the desired product is low due to the formation of various kinds of by-products, (ii) the clogging of the reactor caused by the by-produced polymers occurs due to the carbonization of the by-produced polymers formed upon contact of the propylene with chlorine and also clogging of the heat exchanger is caused by the deposition of the by-produced polymers when quenching the gaseous reaction product by a solvent, and (iii) the equipment is severely corroded due to the handling of hydrogen chloride at an elevated temperature.

Furthermore, in the above-mentioned step (2), since the solubility of the allyl chloride in water is low, the oil phase is formed when the concentration of the allyl chloride is intended to be increased. When the reaction is carried out in this condition, the chlorine is dissolved in the oil phase and the addition reaction of the chlorine to the allyl chloride proceeds in preference to the desired reaction of the allyl chloride with water. As a result, the side reaction of forming trichloropropane is increased. In order to suppress this side reaction, the reaction should be carried out at a low concentration of allyl chloride, which, however, results in the production of the desired dichloropropanol as a low concentration solution thereof.

When the dichloropropanol is obtained at a low concentration, an excessive amount of energy is required in the above-mentioned step (3). That is, when the desired epichlorohydrin is stripped with steam while the saponification of the reaction equation (3) is carried out, extra energy (i.e., heat energy corresponding to the sensible heat) is required for increasing the temperature of the low concentration solution of dichloropropanol and an excessive amount of steam is required for stripping the desired epichlorohydrin due to the low concentration thereof.

Furthermore, since the dichloropropanol formed in the above-mentioned reaction equation (2) is obtained in the form of a mixture of two isomers (i.e., 1,3-dichloro product and 2,3-dichloro product), the saponification conditions of both isomers cannot be optimized at the same time because the saponification reaction rates of the isomers are extremely different. As a result, the improvement in the yield of the desired epichlorohydrin is naturally limited. In addition, in the above-mentioned conventional process, a large amount of lime is unpreferably consumed for neutralizing hydrogen chloride formed in an equimolecular amount in the reaction equation (2).

Various attempts have been proposed to improve the above-mentioned problems or disadvantages. For example, the process represented by the following reaction equation (4) to (7) is disclosed in Khim. Prom. No. 6, 328–335 (1982).

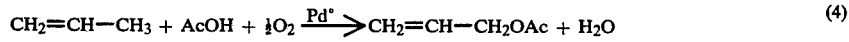

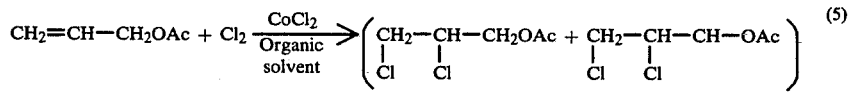

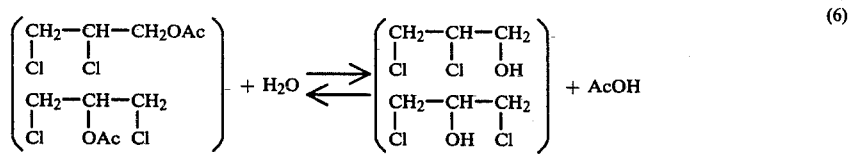

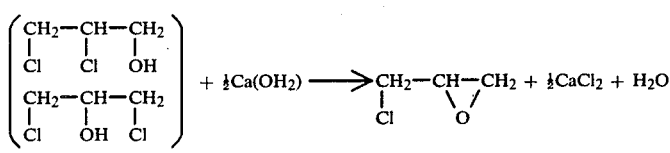

However, these reactions still have various problems or disadvantages from the practical point of view, although this process is advantageous in that the reaction can be carried out at a higher concentration when compared to the above-mentioned case. For example, in the above-mentioned chloroation reaction step (5), the CoCl$_2$ catalyst must be separated after the reaction. In addition, the yield of the desired product is not high (e.g., 47.5% to 84.2%) and, therefore, the unreacted allyl acetate should be separated and recovered. Furthermore, side reactions such as a substitution reaction with chlorine occurs and, accordingly, the methyl group of the acetyl group is, for example, chlorinated, so that the acetic acid is wastefully consumed and allyl chloride is formed as a by-product. The resultant chlorinated product is obtained as a mixture of the 2,3-dichloro isomer and 1,3-dichloro isomer and, therefore, the yield of the desired product in the saponification step is naturally limited. Furthermore, although the organic solvent used in the reaction (5) must be recovered, a portion of the organic solvent is inevitably lost during the distillation.

In the above-mentioned reaction step (6), the reaction is an equilibrium reaction and, therefore, the H$_2$O ratio of the dichloropropyl acetate to the dichloropropanol should be increased to increase the conversion rate. However, since the starting dichloropropyl acetate has the highest boiling point in the equilibrium system, all the reaction mixture including water, as well as the reaction products such as acetic acid and dichloro propanol, must be vaporized to recover the unreacted dichloropropyl acetate for the purpose of recycling. This means that a large amount of heat energy is required for increasing the conversion of the reaction (6). Furthermore, although a by-product obtained by chlorinating the acetyl group in the chlorination reaction (5) is converted to monochloro acetic acid in the hydrolysis reaction (6), the separation thereof from the desired 2,3-dichloro-1-propanol is difficult because the boiling point of monochloro acetic acid is 187° C., which is close to that of 2,3-dichloro-1-propanol.

In the above-mentioned saponification reaction (7), the optimization of the reaction conditions is difficult due to the difference in the reaction rates between the 2,3-dichloro isomer and the 1,3-dichloro isomer as mentioned above.

Another proposal to improve the problems or disadvantages of the above-mentioned typical conventional case is represented by the following reaction equations (8) to (10) as disclosed in Compend. - Dtsch. Geo. Mineraloelwiss. Kohlchem. p. 318–326 (1975).

(8)

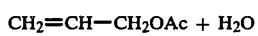

(9)

$$CH_2=CH-CH_2Cl + AcOH$$

$$CH_2=CH-CH_2Cl + Cl_2/H_2O \longrightarrow$$ (10)

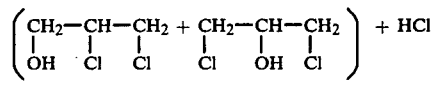

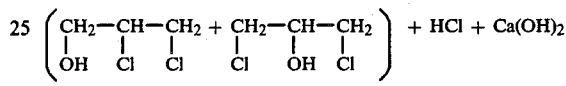

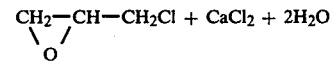

This process is advantageous in that the selectivities of the equations (8) and (9) are about 90% and about 96%, respectively and, accordingly, the selectivity of allyl chloride from propylene is about 86.4%, which is more than 10% higher than that of the conventional process. However, this process still has the following disadvantages:

(i) The reaction (9) should be carried out in the presence of CuCl or FeCl$_2$ catalyst in a non-aqueous system to prevent hydrolysis. Accordingly, the water must be removed from the reaction mixture of the previous reactions (8), which generates the water and is generally carried out in the presence of water.

(ii) The reaction (9) also requires the use of expensive anhydrous hydrogen chloride.

(iii) In order to separate and recover the catalyst from the reaction mixture, the unreacted allyl acetate, the resultant acetic acid, the solvent, and the like should be removed by distillation.

(iv) Since the reaction subsequent to the equation (10) is the same as in the above-mentioned conventional processes, the above-mentioned problems and disadvantages are still involved in this process.

SUMMARY OF THE INVENTION

An object of the present invention is to eliminate the above-mentioned disadvantages or problems of the prior art and to provide a process for industrially advantageously producing epichlorohydrin.

Other objects and advantages of the present invention will be apparent from the following description.

In accordance with the present invention, there is provided a process for producing epichlorohydrin comprising the steps of:

(a) reacting allyl alcohol with chlorine at a temperature of $-30°$ C. to 20° C. under a pressure of 0 to 10 atm.(gauge) in an aqueous hydrogen chloride solution containing more than 45% but not more than 70% by weight of hydrogen chloride to form 2,3-dichloro-1-propanol;

(b) separating at least a portion of hydrogen chloride by heating the reaction mixture obtained at step (a) to recover the hydrogen chloride in the form of gas;

(c) recycling the hydrogen chloride recovered at step (b) to step (a);

(d) separating the resultant liquid mixture after recovering at least a portion of the hydrogen chloride at step (b) into an aqueous phase and an oil phase by cooling the resultant liquid mixture to a temperature of 40° C. or less;

(e) recycling at least a portion of the separated aqueous phase step (d) to step (a); and (f) reacting the oil phase separated at step (d) directly or after increasing the purity of 2,3-dichloro-1-propanol contained in the oil phase by a separation operation with an aqueous alkaline solution or suspension at a temperature of 40° C. to 110° C. to form epichlorohydrin.

BRIEF DESCRIPTION OF THE DRAWING

The present invention will be better understood from the description set forth below with reference to the accompanying drawing of FIG. 1, which schematically illustrates the flow of the preferred embodiment of the present process.

DESCRIPTION OF THE PREFERRED EMBODIMENTS

Figure 1:
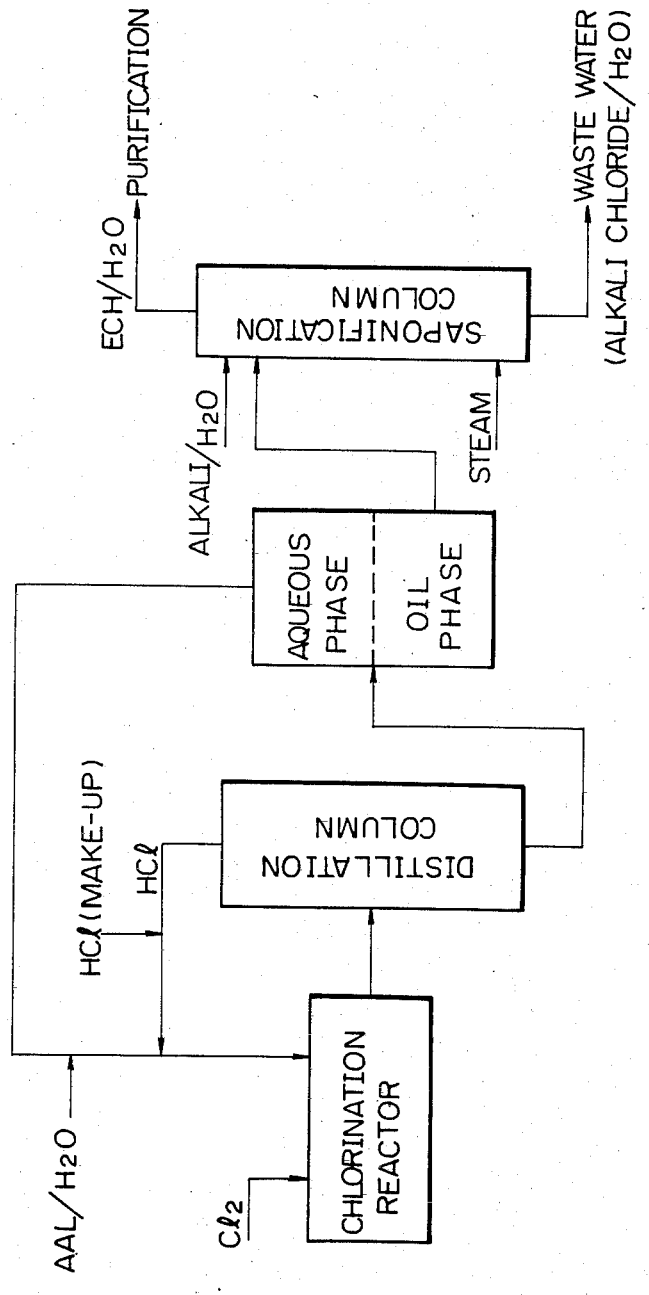

According to the present invention, the desired epichlorohydrin can be prepared from the following reaction equations from propylene.

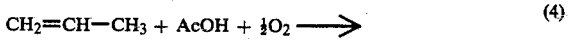

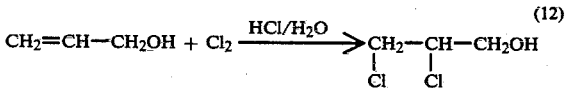

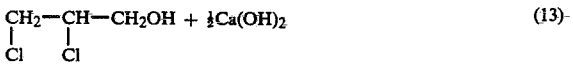

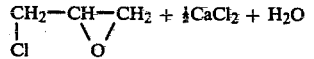

(I) Production of Starting Allyl Alcohol (i.e., Equations (4) and (11))

As shown in equation (4), propylene, oxygen or oxygen-containing gas, and acetic acid are reacted in the presence of, as a catalyst, alkali acetate and palladium and, optionally, a copper compound supported on a carrier in a vapor phase, e.g., at 100° C. to 300° C. and 0 to 30 atm (gauge), to obtain the desired allyl acetate as disclosed in, for example, Japanese Unexamined Patent Publication (Kokai) No. 60-32747. The allyl acetate thus formed is cooled to collect the desired product and a homogenous mixture is prepared by adding an aqueous acetic acid solution to the collected product. The homogenous mixture is passed through a tubular reactor packed with strongly acidic ion exchange resin and heated with a heating medium. The resultant reaction mixture is distilled to obtain an aqueous high concentration solution of allyl alcohol.

(II) Chlorination Reaction (i.e., Equation (12))

Hitherto, various processes have been proposed to produce 2,3-dichloro-1-propanol from the chlorination of allyl alcohol with molecular chlorine. For example, at the beginning, water-free allyl alcohol was chlorinated with dry chlorine without using a solvent, as disclosed in, for example, Tornoe, Ber., 24, 2670 (1891). The chlorination is carried out using carbon disulfide solvent as disclosed in, for example, J. Chem. Soc., 105, 1238 (1914). However, the yield of the 2,3-dichloro-1-propanol in these processes is approximately 20% to 40%.

On the other hand, Japanese Unexamined Patent Publication (Kokai) No. 46-1361 discloses a process for producing dichloro propanol at a high yield (e.g., 97% to 99%) by using a hydrogen chloride saturated solution of an ether having a low boiling point. However, a mixture of approximately 10% by weight of 1,3-dichloro-2-propanol contained in the desired 2,3-dichloro-1-propanol is formed in this process, and the problems of the separation from the solvent and the loss of the product and solvent during the distillation purification still remain. Japanese Examined Patent Publication (Kokoku) No. 48-18207 discloses, as a process for producing 2,3-dichloro-1-propanol without forming as a by-product 1,3-dichloropropanol, that the desired 2,3-dichloro-1-propanol is obtained by using, as a solvent, lower aliphatic alcohol saturated with hydrogen chloride at a high yield (e.g., 96.9% at −40° C., 93.8% at 0° C.). However, also in this case, the above-mentioned problems of the separation of the desired product from the solvent and the loss of the solvent remain.

In addition, Japanese Examined Patent Publication (Kokoku) No. 37-17206 discloses a process for producing the desired 2,3-dichloro-1-propanol by effecting the chlorination in an aqueous solution saturated with hydrogen chloride without using an organic solvent. However, although it is disclosed that 1,3-dichloro-2-propanol is not produced as a by-product, the yield is only 50% to 70%, and glycerol monochloride and oligomers are disadvantageously produced as by-products.

Contrary to the above, in the chlorination step according to the present invention, it has been found that the desired 2,3-dichloro-1-propanol can be obtained at a yield of 90% or more substantially without producing 1,3-dichloro-2-propanol as a by-product when the chlorination is carried in an aqueous solution having a hydrogen chloride concentration of more than 45% by weight but not more than 70% by weight. That is, the chlorination step according to the present invention is characterized by using, as a solvent, an aqueous hydrogen chloride solution having a hydrogen chloride concentration of more than 45% by weight but not more than 70% by weight, preferably, 50% to 60% by weight, in the production of the desired 2,3-dichloro-1-propanol from the reaction of allyl alcohol with chlorine.

As is well known in the art, the maximum hydrogen chloride concentration in the hydrochloric acid solution at an ambient temperature and pressure is about 36% by weight. Accordingly, in order to maintain the hydrogen chloride concentration in an aqueous solution at more than 45% by weight, the temperature of the aqueous solution should be decreased or the pressure of the aqueous solution should be increased. However, since the starting allyl alcohol is present together with the hydrogen chloride in the reaction system according to the present invention, it is not difficult to maintain the high concentration of the hydrogen chloride in the reaction mixture, when compared to the system consisting of water and hydrogen chloride.

In order to maintain the hydrogen chloride concentration in the aqueous solution at more than 45% by weight, the chlorination according to the present invention is carried out at a temperature of $-30°$ C. to $20°$ C., preferably $-15°$ C. to $10°$ C., under a pressure of 0 to 10 atm (gauge), preferably 0 to 5 atm (gauge). When allyl alcohol is chlorinated in an aqueous solution having the above-mentioned elevated concentration of hydrogen chloride according to the present invention, the production amount of the undesired by-products such as glycerol monochloride and oligomers can be remarkably decreased. However, the use of too high an amount of hydrogen chloride under too high a pressure causes the undesired increase in the production amount of other by-products, especially 1,2,3-trichloropropane and allyl chloride. This tendency becomes remarkable with the increase in the reaction temperature. However, when the reaction temperature is not more than $20°$ C. and the reaction pressure is not more than 10 atm (gauge), the formation of the undesired by-products can be substantially eliminated.

Although the yield of the desired product is increased with the decrease in the reaction temperature in the present process, the use of too low a reaction temperature causes the undesirable increase in the cooling energy and sometimes causes the solidification of the reaction mixture, depending upon the composition of the reaction mixture. Accordingly, the reaction is preferably carried out at a temperature of $-20°$ C. or more. Although there is no critical concentration of the starting allyl alcohol, the allyl alcohol is preferably used in an amount such that the total amount of the allyl alcohol and the desired product, 2,3-dichloro-1-propanol is 0.1 to 5 parts by weight based on 1 part by weight of water. The pressure during the reaction corresponds to the vapor pressure of the dissolved HCl in the reaction mixture at the reaction temperature and, therefore, largely depends upon, for example, the composition and temperature of the reaction mixture.

In the chlorination step according to the present invention, the amount of chlorine consumed in the reaction can be about 1.05 mol or less based on 1 mol of the allyl alcohol. Thus, the desired 2,3-dichloro-1-propanol can be almost quantitatively obtained from the allyl alcohol. Thus, the yield of the desired product in the present chlorination step is increased by 20% or more when compared with that of the conventional method (i.e., about 72%).

According to the present chlorination step, a portion of the hydrogen chloride is recovered by heating the reaction mixture in an HCl recovery column and the recovered hydrogen chloride is recycled to the chlorination step (or the chlorination reactor), as shown in FIG. 1. Thus, since hydrogen chloride and water are azeotropically distilled at a hydrogen chloride concentration of about 20% by weight, the hydrogen chloride present in excess over the azeotropic composition is readily recovered as gaseous hydrogen chloride. When the resultant liquid mixture is cooled to a temperature of $40°$ C. or less, the liquid mixture is separated into an upper aqueous phase or layer and a lower oil phase or layer. The aqueous phase contains a large part of the aqueous hydrochloric acid (e.g., about 80%) and the remainder of the other components, such as a small amount of 2,3-dichloropropanol. The lower oil phase contains a large part of the resultant 2,3-dichloropropanol (e.g., about 80%) and the remainder of the other components, such as water and a small amount of hydrogen chloride. The aqueous phase is recycled after separation as a solvent to the chlorination step as illustrated in FIG. 1. The oil phase is used in the subsequent saponification step, directly or after recovery of the 2,3-dichloro-1-propanol by distillation.

Advantageous Features of Present Chlorination Step

As mentioned above, according to the present chlorination step, the desired 2,3-dichloro-1-propanol is obtained at a high selectively. Furthermore, the chlorination does not suffer at all from the problems found in the conventional processes, such as separation from the organic solvent, contamination of the desired product with the solvent, and loss of the desired product and solvent during distillation.

(III) Saponification Step

The saponification reaction itself according to the present invention is the same as in the conventional processes. That is, the dichloropropanol is reacted with an alkali such as lime, sodium hydroxide, or potassium hydroxide to form the desired epichlorohydrin. The reaction is generally carried out at a dichlopropanol concentration of 10% to 50% by weight at a temperature of $40°$ C. to $110°$ C., preferably $60°$ C. to $100°$ C., under a reduced pressure or under pressure, by using an alkali in an amount of 1.0 to 1.5 equivalents, preferably 1.03 to 1.3 equivalents, based on 1 mol of dichloropropanol. When the reaction is carried out at a low temperature, a reduced pressure is preferably used. The above-mentioned amount of the alkali used is the amount when 100% of the dichloropropanol is intended to be reacted. When the reaction is suppressed below 100%, the amount of the alkali may be in the amount above-mentioned, based on the intended amount of the dichloropropanol to be reacted.

The saponification reaction according to the present invention can be carried out in various ways. Examples of such reactions are as follows.

(1) The starting dichloropropanol and lime milk slurry are fed to the top of a plate type distillation column, while steam is fed from the bottom of the column, as illustrated in FIG. 1. The azeotropic mixture of the resultant epichlorohydrin and water is boiled at a boiling point of $88°$ C. Thus, the desired epichlorohydrin is stripped. In this method, the stripping effect can be increased by accompanying the steam with an inert gas such as nitrogen.

(2) The 2,3-dichloropropanol or an aqueous solution thereof is mixed with lime milk in a liquid phase, while stirring. Thus, the saponification reaction is carried out.

(3) The saponification reaction is carried out in the presence of an inert solvent substantially insoluble in water, such as hydrocarbons (e.g., benzene, toluene) and halogenated hydrocarbons (e.g., 1,2-dichloroethane and 1,2,3-trichloropropane), while the formed epichlorohydrin is extracted with the solvent.

The above-mentioned methods (2) and (3) can be carried out in either a continuous or batchwise manner. Either of a mixing vessel type reaction or a flowthrough type reaction using a column type reactor may be used for the continuous reaction. In the latter case, the starting 2,3-dichloro-1-propanol or the aqueous solution thereof and lime milk may be brought into contact with each other either in a parallel flow or in a counter flow. Furthermore, after the saponification reaction is effected to a certain extent in the above-mentioned reaction method (2) or (3), a further reaction can be carried out by another method.

Characteristic Feature of Saponification Step of Present Invention

The saponification step according to the present invention has the following characteristic features.

(1) Since only one component, 2,3-dichloro-1-propanol is saponified in the present saponification process, the optimum reaction conditions can be readily selected.

That is, when 1,3-dichloro-2-propanol is included as in the above-mentioned conventional processes, the optimum saponification conditions cannot be selected since the saponification reaction rate constant of the 1,3-dichloro isomer with $Ca(OH)_2$ is larger by about 30 times than the 2,3-dichloro isomer. This is because, when the reaction conditions are adapted to the 1,3-dichloro isomer, the desired saponification of the 2,3-dichloro isomer cannot be completely effected and, therefore, the unreacted 2,3-dichloro isomer is included in the waste liquid. This causes unpreferable loss of the 2,3-dichloro isomer and also causes a waste liquid treatment problem. Contrary to this, when the saponification reaction conditions are adapted for the 2,3-dichloro isomer, the saponification conditions become severe for the 1,3-dichloro isomer, since the reaction time period is too long or the reaction temperature is too high, and unpreferable side reactions such as the hydrolysis of the desired epichlorohydrin are increased. Thus, the yield of the desired epichlorohydrin is limited.

The above-mentioned problems of conventional processes are not involved in the present saponification process and, therefore, the desired epichlorohydrin can be advantageously obtained at a high yield according to the present invention.

(2) According to the present invention, since the starting 2,3-dichloro-1-propanol is obtained at a high concentration with a minimum energy loss in the previous step, the following advantageous features can be obtained.

(a) When the saponification is carried out according to the above-mentioned stripping method, the energy for increasing the temperature of the reaction mixture can be minimized and the energy for stripping also can be minimized due to the high stripping efficiency. In the case of the above-mentioned extracting saponification method, the energy for increasing the temperature of the reaction mixture can be saved and the extraction efficiency is high. Furthermore, in either case, the yield of the reaction is increased when compared with the conventional methods.

(b) Since the total amount of the reaction mixture becomes small, the reaction apparatus can be made small and compact.

(3) As mentioned above, according to the conventional processes, 1 mol of HCl based on 1 mol of the dichloropropanol, which is produced as a by-product in the previous chlorohydrination step, is included in the starting material of the saponification step. However, according to the present invention, HCl is not produced as a by-product in the previous step, and the wasteful consumption of the alkali for the neutralization does not occur in the present invention.

EXAMPLE

The present invention will now be further illustrated by, but is by no means limited to, the following Example.

(1) Production of Starting Allyl Alcohol

A 500 ml amount of a catalyst comprising palladium, copper, and potassium acetate supported on silica and having a particle size of 2 to 3 mm was packed into a stainless steel reaction tube having an inner diameter of 28 mm. A gas mixture of 50.8% of $N_2$, 25% of propylene, 4.9% of oxygen, 5.3% of acetic acid, and 14% of water (all by volume) was fed to the reaction tube at a feed rate of 1.2 $NM^3$/hr. The reaction was carried out under a pressure of 4.5 atm (gauge). The reaction temperature was controlled with an oil bath in such a manner that the maximum temperature in the inside of the reaction tube under a steady state became 176° C. The amount of allyl acetate in the resultant reaction gas was 205 g/hr. This corresponds to a selectivity of 95.7% based on the reacted amount of the starting propylene.

The allyl acetate obtained above was collected by cooling the reaction gas and a homogeneous solution was obtained by adding an aqueous acetic acid thereto. The composition of the solution was 27.6% of allyl acetate, 35.0% of acetic acid, and 37.0% of water (all by weight).

The solution was fed to a glass reaction tube having an inner diameter of 25 mm and packed with 500 ml of a strongly acidic ion exchange resin ($H^+$ type) at a rate of 1000 g per hour with a constant metering pump and the reaction was carried out while the liquid level was kept constant. The reaction temperature was kept constant at a temperature of 80° C. by circulating a heating medium through a jacket provided on the outside of the reaction tube.

The composition of the effluent liquid was 14.1% of allyl acetate, 43.2% of acetic acid, 34.5% of water, and 7.9% of allyl alcohol (all by weight). The resultant hydrolyzed solution was distilled to obtain an 81% by weight aqueous solution of allyl alcohol.

(2) Chlorination of Allyl Alcohol

By using the 81% by weight aqueous solution of allyl alcohol obtained in (1) above as a starting material, the chlorination reaction, the separation and recovery of hydrogen chloride, and the separation of the 2,3-dichloro-1-propanol rich oil phase were continuously carried out as follows.

The apparatus used was a hydrogen chloride dissolving vessel in which hydrogen chloride is dissolved to a saturated condition in a mixture of allyl alcohol and a 35% aqueous hydrochloric acid, a first stage reactor, a second stage reactor, a distillation column for separating gaseous hydrogen chloride from the reaction mixture, and a decanter for separating the liquid from the distillation column into an aqueous phase and an oil phase.

The hydrogen chloride dissolving vessel was provided with a cooler for removing the dissolution heat. In this vessel, gaseous hydrogen chloride discharged from the distillation column is fed to a mixture of allyl alcohol and a 35% aqueous hydrochloric acid. Thus, the starting liquid mixture saturated with the dissolved hydrogen chloride was obtained. The first stage reactor used was made of glass and had a volume of 300 ml. The first stage was provided with a stirrer, a thermometer, a liquid feel nozzle for a starting material (i.e., aqueous allyl alcohol solution saturated with hydrogen chloride), a gas feed nozzle for gaseous chlorine, and an outlet for discharging the reaction mixture. The temperature was controlled by means of an outer heating jacket and an inner cooling pipe. The gaseous chlorine was fed into the liquid through a sparger. The reaction mixture was withdrawn in an overflow fashion so as to keep the liquid level constant and fed the liquid to the second stage reactor.

The particulars of the second stage reactor were similar to those of the first stage reactor, except that the volume thereof was 500 ml. The liquid mixture discharged from the second stage reactor was fed to the distillation column. The distillation column had a bottom volume of 100 ml, an inner diameter of 32 mm, and a height of 50 cm, and the bottom was heated with an oil bath. A constant amount of the bottom liquid was discharged from the bottom of the distillation column by means of a pump and was fed to the decanter. The top of the distillation column was connected to the hydrogen chloride dissolving vessel so that the hydrogen chloride was recycled.

The decanter was cooled with an outside jacket. The upper layer (i.e., aqueous phase) was discharged by a constant metering pump and was recycled to the hydrogen chloride dissolving vessel, and the lower layer (i.e., oil phase) was withdrawn by a constant metering pump and was sent to the subsequent saponification step.

The experimental results obtained in the above-mentioned apparatus were as follows.

At the beginning of the experiment, fresh gaseous hydrogen chloride was supplied from a gas bomb to saturate the allyl alcohol solution with the dissolved hydrogen chloride. However, after the hydrogen chloride was started to be recycled from the distillation column and the decanter, the 35% hydrochloric acid fed therefrom was supplied. The recycling of the hydrogen chloride and the aqueous phase of the decanter as well as the other system, were stabilized, and the following results were obtained.

A 50.2 g/hr amount of 81% by weight aqueous allyl alcohol, 13.8 g/hr of 35% aqueous hydrochloric acid, and 114.2 g/hr of the recycled liquid from the decanter were separately fed to the hydrogen chloride dissolving vessel by means of constant metering pumps. While the recycled hydrogen chloride from the distillation column was dissolved, the temperature was kept at 0° C. The composition of the starting reaction mixture from the hydrogen chloride dissolving vessel was 35.9% of hydrogen chloride, 34.9% of water, 16.6% of allyl alcohol, and 11.1% of 2,3-dichloro-1-propanol (all by weight). This starting mixture was fed to the first stage reactor. To the first stage reactor, 39.8 g/hr (i.e., 12.6 Nl/hr) of gaseous chlorine was fed. The reaction temperature was kept at 0° C. and the hold amount of the reactor was kept to 140 ml. The retention time was about 40 minutes.

To the second stage reactor, 15.2 g/hr of gaseous chlorine was fed, while the reaction temperature was kept at 0° C. and the liquid hold amount was kept to 300 ml. The retention time was about 80 minutes.

All the allyl alcohol was reacted at the outlet of the second stage reactor. The composition at the outlet of the second stage reactor was 38.0% of 2,3-dichloro-1-propanol, 2.0%, in total, of 3-chloro-1,2-propane diol and 2-chloro-1,3-propane diol, 30.0% of HCl, 29.0% of water, and 1.0% of the other components (all by weight).

The liquid mixture fed to the distillation column was withdrawn from the bottom thereof at a temperature of 110° C. under an ambient pressure and was fed to the decanter. The decanter was kept at a temperature of 30° C. The upper and lower layers separated in the decanter were separately withdrawn. The upper layer (i.e., aqueous phase) was recycled to the hydrogen chloride dissolving vessel. The amount of the lower layer (i.e., oil phase) withdrawn from the decanter was 112 g/hr and contained 76.7% of 2,3-dichloro-1-propanol, 4.3% of hydrogen chloride, and 16.2% of water (all by weight). The yield of the desired 2,3-dichloro-1-propanol in this step was 95.0%.

(3) Production of Epichlorohydrin by Saponification of 2,3-Dichloro-1-Propanol

The 2,3-dichloro-1-propanol solution obtained in step (2) above was directly used as a starting material for the saponification reaction. The saponification column used for simultaneously carrying out the hydrochloric acid removal reaction of the dichloropropanol and the stripping of the formed epichlorohydrin from the reaction mixture immediately after the formation was as follows.

The column was made of glass and had an inner diameter of 55 mm$\phi$ and a height of 1500 mm. In the column, 10 perforated plates having 280 holes with a size of 1 mm$\phi$ and a downcomer having a depth of 5 mm were placed with a plate distance of 100 mm. The steam feed nozzle was opened below the lowermost plate so that a constant amount of steam could be fed to the column through a flow meter. The liquid feed nozzle was opened above the uppermost plate so that the dichloropropanol and an aqueous alkali solution were fed to the column. The dichloropropanol and the aqueous alkali solution were sent by constant metering pumps and were mixed together immediately before the liquid feed nozzle. From the top of the column, the distilled liquid was collected through a cooler. A 500 ml round bottom flask was attached to the bottom of the column and the bottom liquid was discharged by a constant metering pump so as to keep the discharge volume of the bottom liquid to 40 ml.

By using the above-mentioned apparatus, 85.3 g/hr of 2,3-dichloro-1-propanol and 32.3 g/hr of a 9.5% by weight aqueous Ca(OH)$_2$ slurry were fed to the column from the liquid feed nozzle, while steam was fed through the steam feed nozzle. The concentration of 2,3-dichloro-1-propanol in the feed liquid was 20% by weight. While the waste liquid was withdrawn from the bottom of the column, the continuous operation was carried out for about 2 hours. Thus, the reaction system was made steady. After one hour, the distilled liquid from the top of column and the bottom liquid of the column were sampled. The temperature of the intermediate plate portion of the column was 100° C. The analytical results were as follows.

Conversion of 2,3-dichloro-1-propanol: 88.2%*²
Selectivity of epichlorohydrin: 97.0%*²
Selectivity of glycerol: 1.9%
Selectivity of the other products: 1.1%
Ratio of H₂O/epichlorohydrin distilled from the top of column: 1.5

*¹ $\text{Conversion} = \left(1 - \frac{\text{2,3-dichloro-1-propanol in distillate}}{\text{2,3-dichloro-1-propanol in feed liquid}}\right) \times 100$

*² $\text{Selectivity} = \frac{\text{moles of epichlorohydrin produced}}{(\text{moles of 2,3-dichloro-1-propanol fed}) \times (\text{conversion})} \times 100$

We claim:

1. A process for producing epichlorohydrin comprising the steps of:
    (a) reacting allyl alcohol with chlorine at a temperature of $-30°$ C. to $20°$ C. under a pressure of 0 to 10 atm (gauge) in an aqueous hydrogen chloride solution containing more than 45% but not more than 70% by weight of hydrogen chloride to form 2,3-dichloro-1-propanol;
    (b) separating at least a portion of the hydrogen chloride by heating the reaction mixture obtained at step (a) to recover the hydrogen chloride in the form of gas;
    (c) recycling the hydrogen chloride recovered at step (b) to step (a);
    (d) separating the resultant liquid mixture after recovering at least the portion of the hydrogen chloride at step (b) into an aqueous phase and an oil phase by cooling the resultant liquid mixture to a temperature of 40° C. or less;
    (e) recycling at least a portion of the separated aqueous phase at step (d) to step (a); and
    (f) reacting the oil phase separated at step (d) directly or after increasing the purity of 2,3-dichloro-1-propanol contained in the oil phase by a separation operation with an aqueous alkaline solution or suspension at a temperature of 40° C. to 110° C. to form epichlorohydrin.

2. A process as claimed in claim 1, wherein the amount of allyl alcohol is such that the total amount of the allyl alcohol and the 2,3-dichloro-1-propanol is 0.1 to 5 parts by weight based on 1 part by weight of the water.

* * * * *